(12) United States Patent
Dunham et al.

(10) Patent No.: US 6,980,623 B2
(45) Date of Patent: Dec. 27, 2005

(54) METHOD AND APPARATUS FOR Z-AXIS TRACKING AND COLLIMATION

(75) Inventors: Bruce Matthew Dunham, Mequon, WI (US); John Scott Price, Milwaukee, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 62 days.

(21) Appl. No.: 10/696,343

(22) Filed: Oct. 29, 2003

(65) Prior Publication Data

US 2005/0094762 A1 May 5, 2005

(51) Int. Cl.[7] ............................................. G21K 1/02
(52) U.S. Cl. ...................... 378/19; 378/136; 378/137
(58) Field of Search ................... 378/4, 19, 16, 378/14, 15, 109, 110, 111, 114, 121, 127, 378/147, 150; 37/119

(56) References Cited

U.S. PATENT DOCUMENTS

| | | | | |
|---|---|---|---|---|
| 5,550,889 | A | * | 8/1996 | Gard et al. .................. 378/113 |
| 5,559,504 | A | | 9/1996 | Itsumi et al. |
| 6,081,576 | A | | 6/2000 | Schanen et al. |
| 6,104,781 | A | * | 8/2000 | Buchmann .................. 378/101 |
| 6,173,039 | B1 | | 1/2001 | Hampel et al. |
| 6,178,226 | B1 | * | 1/2001 | Hell et al. .................. 378/113 |
| 6,198,791 | B1 | | 3/2001 | He et al. |
| 6,256,364 | B1 | | 7/2001 | Toth et al. |
| 6,298,117 | B1 | | 10/2001 | Hampel et al. |
| 6,310,938 | B1 | | 10/2001 | Toth et al. |
| 6,327,331 | B1 | | 12/2001 | Toth et al. |
| 6,359,958 | B2 | | 3/2002 | Toth |
| 6,370,218 | B1 | | 4/2002 | Toth et al. |
| 6,385,279 | B1 | | 5/2002 | Toth et al. |
| 6,411,677 | B1 | * | 6/2002 | Toth et al. .................. 378/147 |
| 6,424,697 | B1 | * | 7/2002 | Zastrow et al. ............. 378/148 |
| 6,652,143 | B2 | * | 11/2003 | Popescu ...................... 378/207 |
| 6,866,419 | B2 | * | 3/2005 | Toth .......................... 378/207 |
| 2001/0031033 | A1 | | 10/2001 | Toth |
| 2002/0021785 | A1 | | 2/2002 | Toth et al. |
| 2003/0097062 | A1 | | 5/2003 | Toth et al. |

* cited by examiner

Primary Examiner—Edward J. Glick
Assistant Examiner—Irakli Kiknadze
(74) Attorney, Agent, or Firm—Carl B. Horton, Esq.; Armstrong Teasdale LLP

(57) ABSTRACT

A method for adjusting a focal spot position during a scan of a computed tomography (CT) imaging system having a z-axis. The CT imaging system includes a detector array having a plurality of detector elements and an x-ray tube configured to direct an x-ray beam towards the detector through an object to be imaged. The method includes turning on the x-ray tube and reading a z-ratio from the detector. A shift in a position of a focal spot of the x-ray tube is then determined utilizing the read z-ratio. The method further includes using a transfer function to determine a compensating electronic deflection value; and applying the electronic deflection value to the x-ray tube as at least one of a deflection voltage or a deflection current to track the focal spot in the z-axis direction.

20 Claims, 9 Drawing Sheets

METHOD AND APPARATUS FOR Z-AXIS TRACKING AND COLLIMATION

BACKGROUND OF THE INVENTION

This invention relates generally to methods and apparatus relating to x-ray imaging systems, and more particularly to methods and apparatus for adjusting focal spot positioning and collimation relative to a target within an imaging tube.

A collimator in a computed tomographic system is a mechanical device that forms a beam for various slice thicknesses. In various configurations, a collimator is used to maintain a proper aperture to minimize radiation dose to a patient. Also in some configurations of CT, the size and position of the focal spot of the radiation beam is dynamically controllable. In particular, modulating focal spot position in an x-direction enables "focal spot wobble," which improves image quality.

At least one known collimator configuration is suitable for forming x-ray beams in VCT systems having coverage of up to about 20 mm at isocenter. However, newer VCT system coverage is expected to increase to between about 20 and 200 mm. Collimator designs suitable for such large system coverage, combined with z-axis tracking requirements, would be both complicated and expensive.

BRIEF DESCRIPTION OF THE INVENTION

Some configurations of the present invention therefore provide a method for adjusting a focal spot position during a scan of a computed tomography (CT) imaging system having a z-axis. The CT imaging system includes a detector array having a plurality of detector elements and an x-ray tube configured to direct an x-ray beam towards the detector through an object to be imaged. The method includes turning on the x-ray tube and reading a z-ratio from the detector. A shift in a position of a focal spot of the x-ray tube is then determined utilizing the read z-ratio. The method further includes using a transfer function to determine a compensating electronic deflection value; and applying the electronic deflection value to the x-ray tube as at least one of a deflection voltage or a deflection current to track the focal spot in the z-axis direction.

In various configurations, the present invention provides a method for adjusting a focal spot position during a scan of a computed tomography imaging system having a z-axis. The computed tomography imaging system includes a detector array having a plurality of detector elements and an x-ray tube configured to direct an x-ray beam towards the detector through an object to be imaged The method includes reading a temperature of the x-ray tube, obtaining calibration data for a focal spot position of the x-ray tube, and utilizing the tube temperature and calibration data to determine voltages to be applied to a cathode of the x-ray tube. The method further includes applying the determined voltage to the cathode of the x-ray tube.

Also, some configurations of the present invention provide a computed tomography imaging system that includes a detector array having a plurality of detector elements, an x-ray tube configured to direct an x-ray beam towards the detector array through an object to be imaged. The x-ray tube and detector array are on a gantry defining a z-axis. The computed tomography system is configured to electronically adjust a focal spot of the x-ray tube in a z-axis direction to perform z-axis tracking.

Furthermore, some configurations of the present invention provide a computed tomography imaging system that includes a detector array having a plurality of detector elements and an x-ray tube configured to direct an x-ray beam towards the detector array through an object to be imaged. The detector array and the x-ray tube are on a gantry defining a z-axis. The computed tomography system is configured to determine a temperature of the x-ray tube and to electronically adjust a focal spot of the x-ray tube in a z-axis direction in accordance with at least the determined temperature to perform z-axis tracking.

It will thus be appreciated that various configurations of the present invention provide z-axis beam tracking suitable for use with volume computed tomography systems having large coverage at isocenter. Moreover, various configurations of the present invention provide z-axis tracking utilizing a combination of electronic focal spot adjustment and mechanical collimator adjustment, wherein the collimator adjustment is simplified as a result of the combination of electronic and mechanical adjustment.

DETAILED DESCRIPTION OF THE INVENTION

Figure 1:
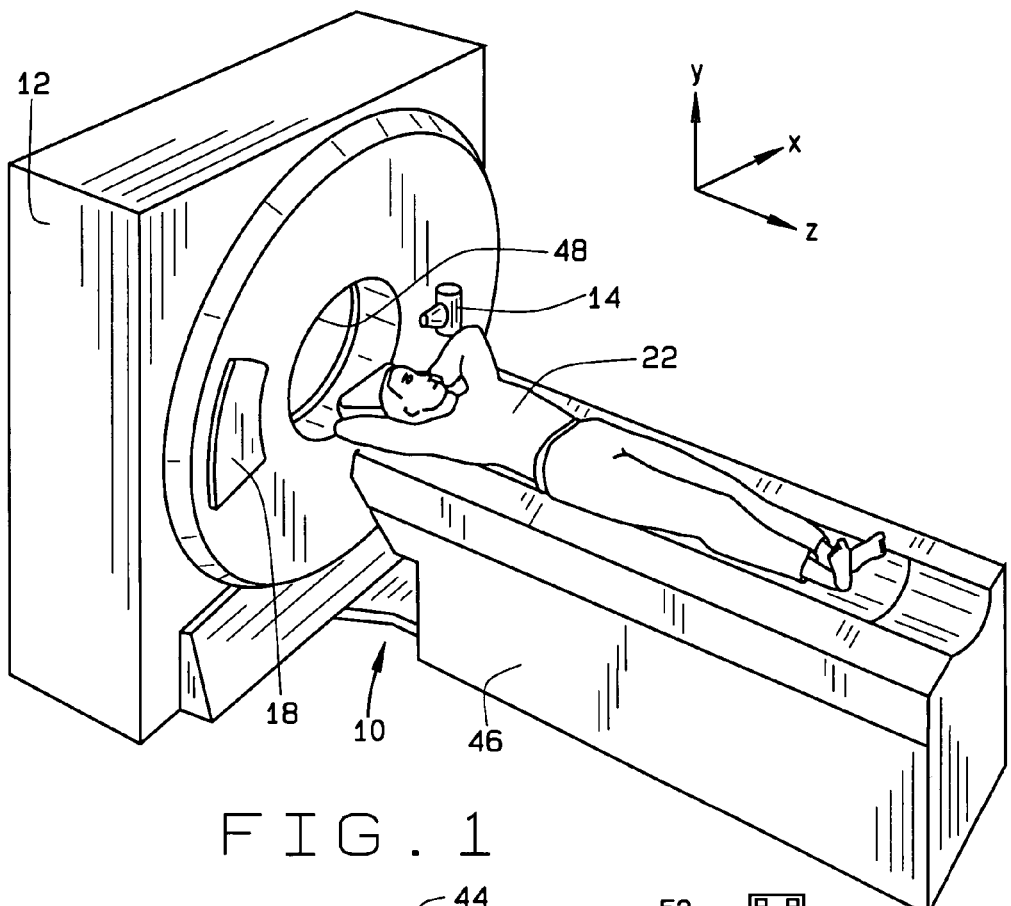
FIG. 1 is a pictorial view of a CT imaging system

Example configurations of systems and methods that perform z-axis tracking and collimation of x-ray imaging systems are described below in detail. A technical effect of the systems described herein include, among other things, facilitating automatic alignment and adjustment of computed tomographic imaging systems.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU). With appropriate further processing, these integers are used to control pixels of an image displayed on an image display device.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
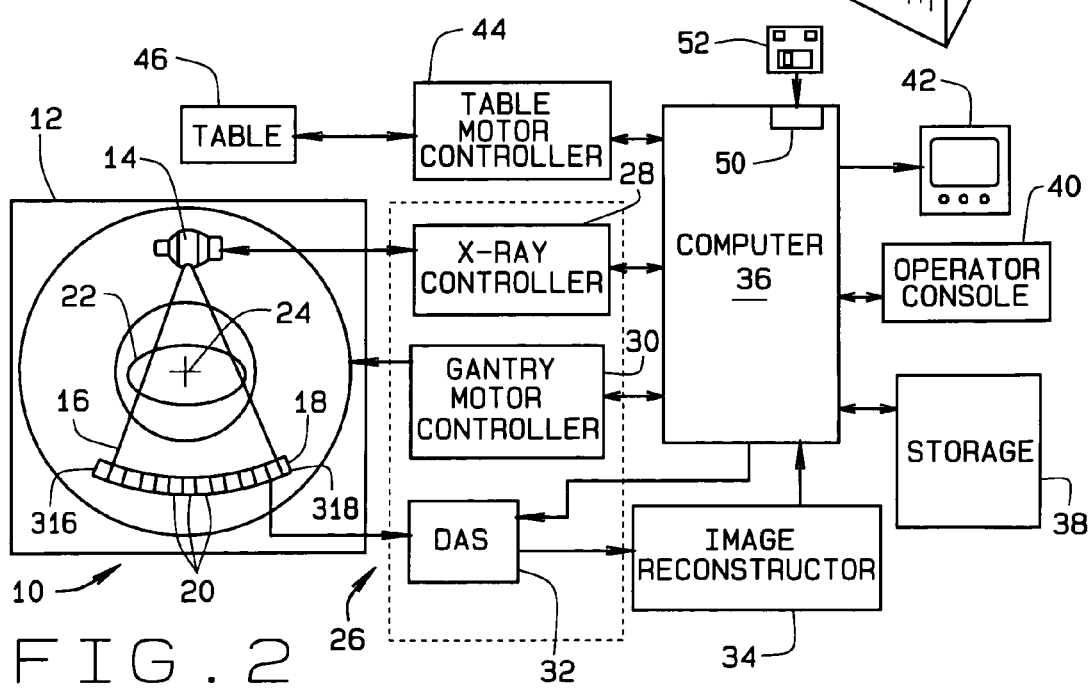
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. The rotation of gantry 12 thus defines a z-axis of imaging system 10. In some configurations, a distributed x-ray source is used. In some of these configurations, gantry 12 rotates only the x-ray source, not detector 18. In some other configurations utilizing a distributed x-ray source, there is no rotatable gantry 12, but the distributed x-ray source generally defines an imaging plane perpendicular to a z-axis essentially parallel to a head-to-toe axis of patient 22 as shown in FIG. 1.

FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan. The amount of coverage provided is a design choice in each embodiment, but in some embodiments can range from between about 20 to about 200 mm at isocenter.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
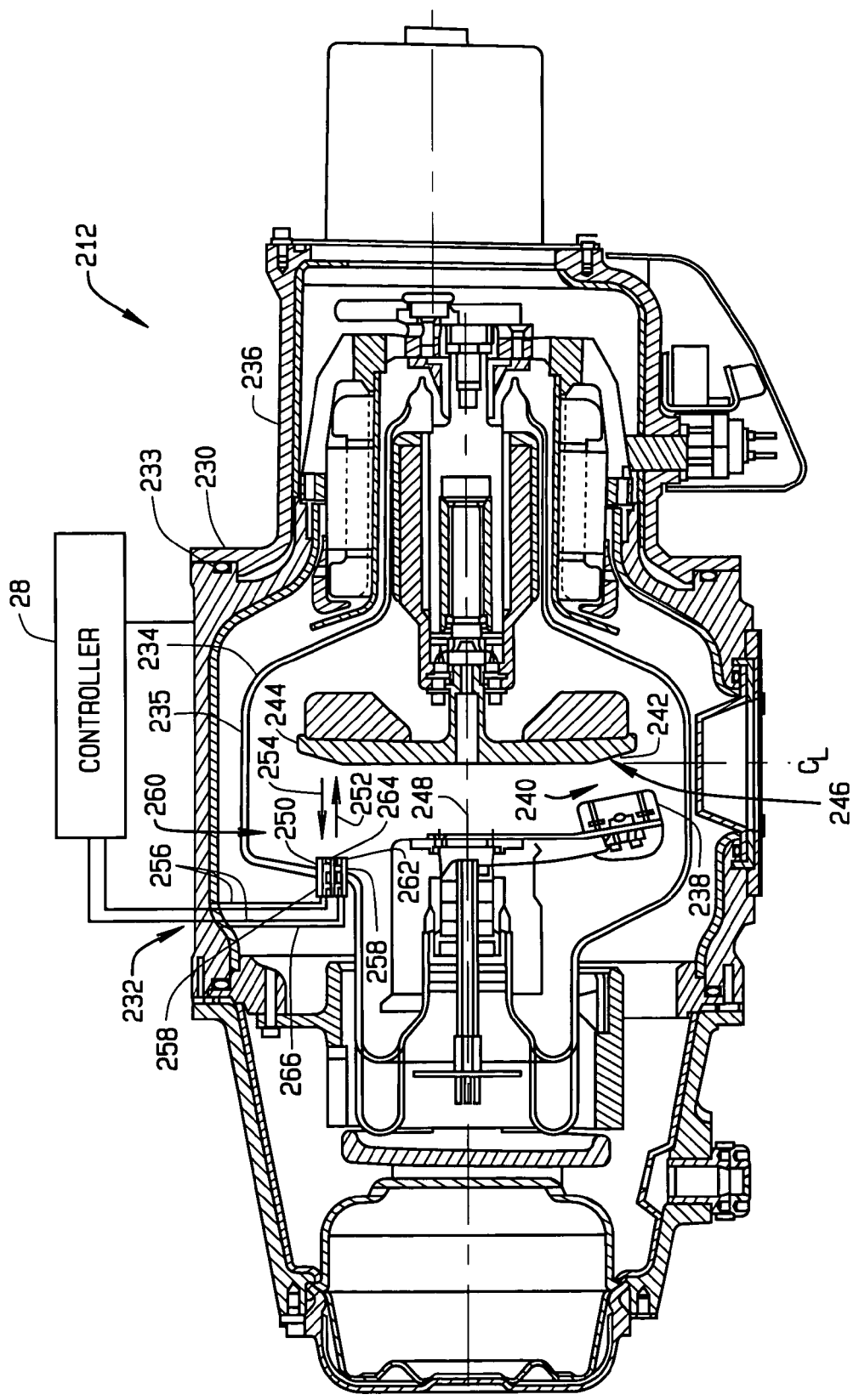
FIG. 3 is a cross-sectional view of configurations of a CT tube assembly including a non-contact x-ray source component position measuring system of the present invention.

Referring now to FIG. 3, a cross-sectional view of a CT tube assembly 230 including a focal spot adjusting system 212 and a non-contact electromagnetic source component position measuring system 232 in accordance with an embodiment of the present invention is shown. Assembly 230 is located within source 18 and includes an x-ray tube 233 having an insert 234. Insert 234 has an insert wall 235 that is within a CT tube housing or casing 236. A cathode 238 generates and emits electrons across a vacuum gap 240 in the form of an electron beam, which is directed at a target 242 that is part of a rotating anode 244 creating a focal spot 246. Anode 244 rotates about a center axis 248.

Position measuring system 232 includes CT tube assembly 230 having a probe 250 directing an emission signal 252 at and receiving a return signal 254 from target 242 for determining position of target 242 relative to casing 236. Emission signal 252 and return signal 254 are in the form of electromagnetic radiation such as visible light, infrared, ultraviolet, radio, or other radiation known in the art. Probe 250 may be directed at and used to determine positioning of other electromagnetic radiation source components. Controller 228 is electrically coupled to probe 250 and generates emission signal 252 and a determines position of target 242 in response to return signal 254 using distance measuring techniques known in the art, such as interferometry or time-of-flight techniques.

In using interferometry to determine distance, emission signal 252 uses an incident wave having a wave front that is fairly uniform at a point of origin. As the wave front is reflected from target 242 it is added with a portion of additionally generated wave fronts, and interference between the originally generated wave fronts and the reflected wave fronts is evaluated for evidence of constructive, partially constructive or destructive interference. In using time-of-flight to determine distance, emission signal 252 is modulated, timed, and delay between transmission of emission signal 252 and reception of return signal 254 indicates distance that emission signal 252 traversed divided by speed of propagation of emission signal 252. Time-of-flight does not require a preserved wave front and is therefore potentially more accurate than interferometry. Reflectivity of emission signal 252, in using both interferometry and time-of-flight, is assured in that metals have high reflectivity over a wide range of wavelengths from near ultraviolet to infrared.

Probe 250 is electrically coupled to controller 28 via a transmission medium 256. Transmission medium 256 in some configurations is an optical conduit formed of fused quartz or other similar materials, such as glass or fiber optic materials known in the art, that are capable of withstanding environmental conditions within tube 233. Fused quartz provides vacuum integrity, resistance to heat, robustness against radiation damage, deformation and transparence to light having a wide range of wavelengths. Standard sealing technology is known in the art for fused quartz and the like. Also, in some configurations, probe 250 includes a plurality of feedthroughs 258. Feedthroughs 258 allow transmission medium 256 to penetrate insert wall 235 into an insert area 260 and seal probe 250, including a first optical conduit end 262 and a second optical conduit end 264, to insert wall 235, and prevent vacuum leakage to the atmosphere.

Probe 250 and feedthroughs 258 in some configurations are located in various locations within CT tube assembly 230 and various configurations have various angular relationships with anode 244. Also in some configurations, probe 250 and feedthroughs 258 are be located such that ends 262 and 264 are positioned opposite to cathode 238 in relation to centerline 248. Thus, ends 262 and 264 are shielded from direct exposure to radiation and focal spot 246, which is typically the hottest portion of anode 244.

A hood or extension tube 266 is utilized in some configurations to further protect transmission medium 256. Extension tube 266 is incorporated as shown encasing transmission medium 256 between casing 236 and probe 250. In some other configurations, extension tube 266 is incorporated so as to protect ends 62 and 64. Extension tube 366 in some configuration comprises stainless steel or other similar material known in the art.

Controller 28 in some configurations is a computer having a central processing unit, memory (RAM and/or ROM), and associated input and output buses. Controller 28 in some configurations is a portion of a central main control unit, while in other configurations, controller 28 is a stand-alone controller as shown.

Figure 4:
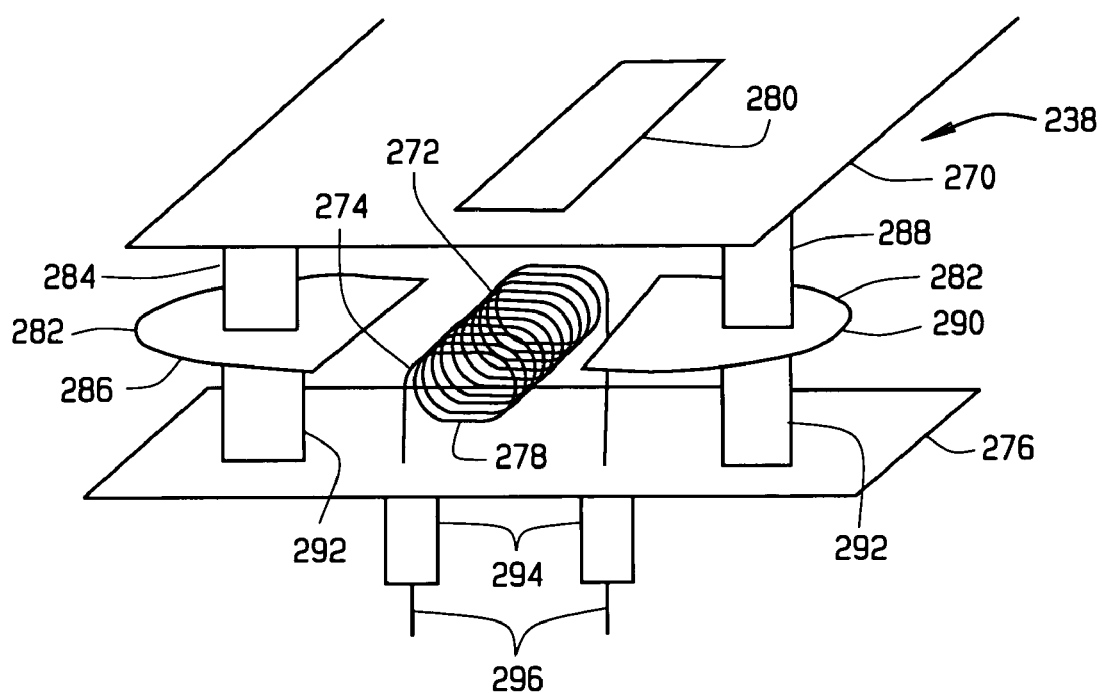
FIG. 4 is a perspective view of a cathode configuration of the present invention.

Referring now to FIG. 4, a perspective view of cathode 238 representative of various configurations of the present invention is shown. Cathode 238 in some configurations includes a front member 270 electrically disposed on a first side 272 of emitter 274 and includes a backing member 276 electrically disposed on a second side 278 of an emitter 274. Front member 270 has an aperture 280 coupled therein. Emitter 274 emits an electron beam to focal spot 246. Aperture 280 and backing member 276 are differentially biased so as to shape and focus the beam to focal spot 246. Deflection electrodes 282 are shown as an electrode pair and are electrically disposed between backing member 276 and front member 270. Deflection electrodes 282 adjust positioning of focal spot 246 on anode 244. Note that cathode 238, as shown, is symmetrical. However, a symmetrical cathode 238 is not required in all configurations of the present invention.

Cathode 238 also includes multiple isolators separating front member 270, backing member 276, and deflection electrodes 282. In some configurations, a first side steering electrode insulator 284 is coupled between front member 270 and a first side steering electrode 286, and a second side steering electrode insulator 288 is coupled between front member 270 and a second side steering electrode 290. First insulator 84 and the second insulator 288 isolate deflection electrodes 282 from front member 270. A pair of backing insulators 292 is coupled between deflection electrodes 282 and backing member 276. Backing insulators 292 isolate deflection electrodes 282 from backing member 276. A pair of filament insulators 294 are coupled to emitter electrodes 296 to maintain emitter 274 at a potential isolated from backing member 276. Deflection electrodes 282 and insulators 284, 286, 288, and 292 may be in various locations and be utilized in various combinations.

Figure 5:
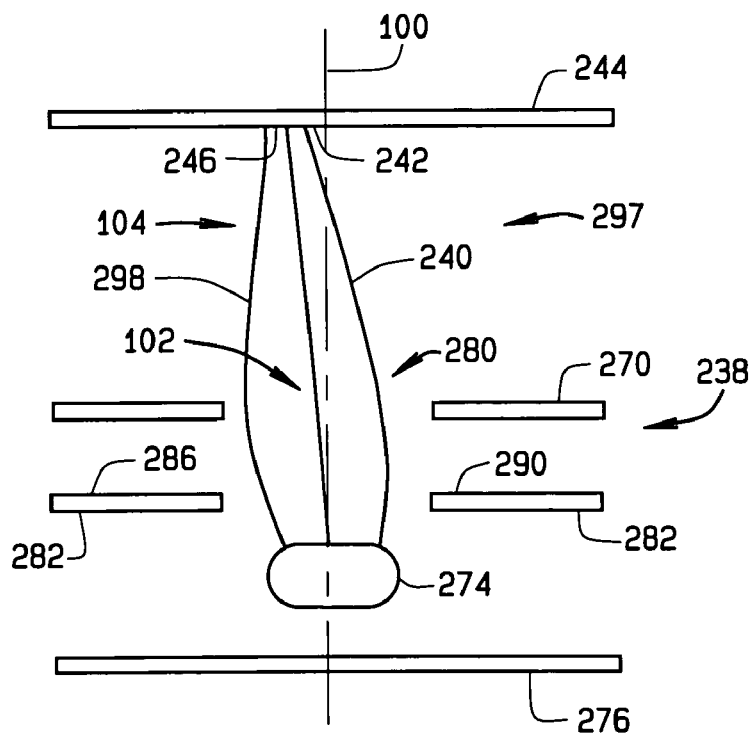
FIG. 5 is a schematic representation of a cathode and an anode configuration of the present invention illustrating an asymmetrical extracted electron beam.

Referring now to FIG. 5, a schematic representation of cathode 238 and anode 244 illustrating an asymmetrical extracted electron beam 240 in various configurations of the present invention is shown. Cathode 238 and anode 244 create a dipole field 297 therebetween. Emitter 274 emits an electron beam 298 through aperture 280 in front member 270 to focal spot 246 on target 242 across dipole field 297. In some configurations, electron beam 298 is symmetrical to an emitter centerline 100 extending through emitter 274 and a center 102 of aperture 280. During focal spot position adjustment, such as during wobbling, deflection electrodes 282 are, in some configurations, asymmetrically biased to adjust position of focal spot 246 on target 242. For example, deflection electrodes 282 are asymmetrically biased to shift focal spot 246 to a left side 104 of emitter centerline 100, as shown.

Bias voltages applied to electrodes 282 are dependent on the specific application. When wobbling, the bias voltages of deflection electrodes 282 are typically less on one side and greater on an opposite side of electrodes 282 as compared to the bias voltage of emitter 274. The bias voltages of deflection electrodes 282 are greater than the bias voltage of backing member 276. In at least one configuration of the present invention, to shift beam 98 to the left, focal spot 246 is adjusted to the left side 104 of emitter centerline 100. Also, an emitter voltage and a front member voltage approximately equal to 0V, a backing member voltage approximately equal to −6 kV, a first electrode voltage approximately equal to 700V, and a second electrode approximately equal to −300V are used. Note that first electrode 86 is positively biased and has a larger bias than second electrode 90, to shift electron beam 298 towards first electrode 286.

Figure 6:
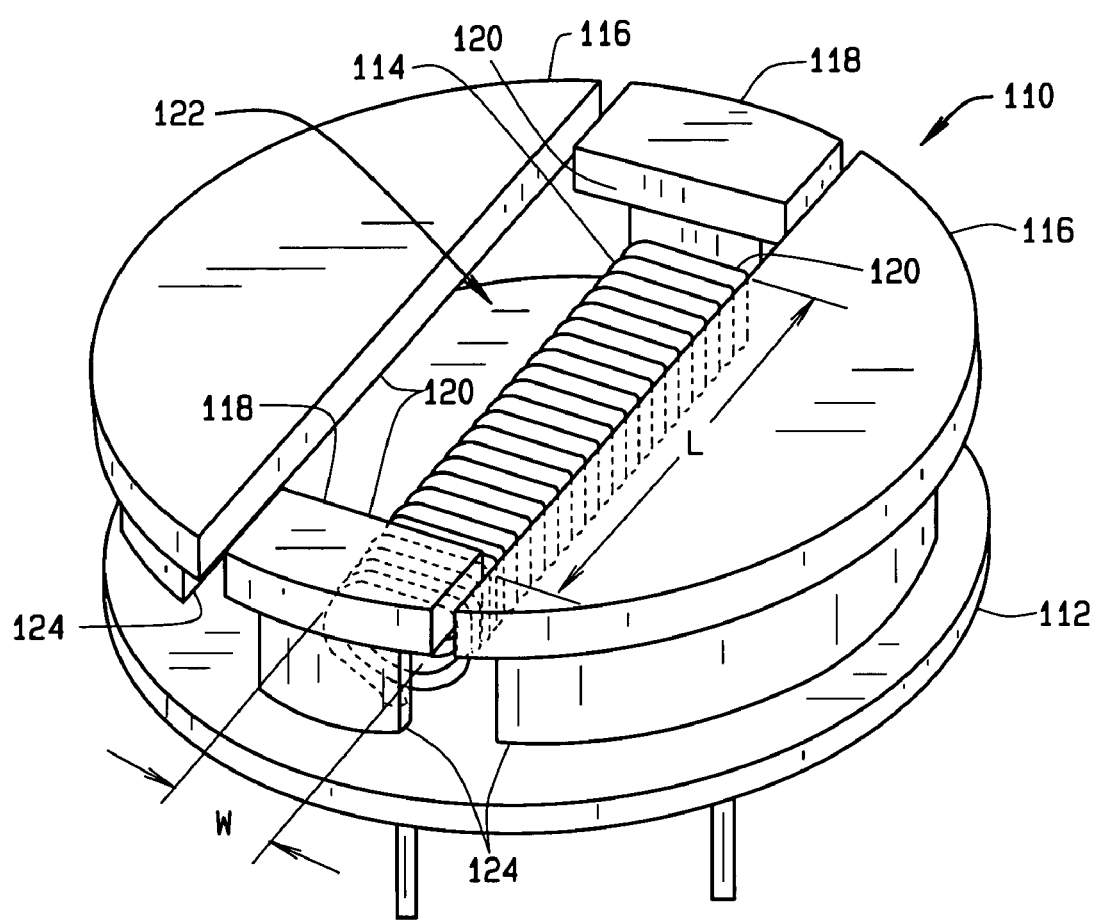
FIG. 6 is a perspective view of another cathode configuration of the present invention.

Referring now to FIG. 6, a perspective view of another configuration of cathode 110 is shown. Cathode 110, similarly to cathode 238, includes a backing member 112 and an emitter 114. A first pair of deflection electrodes 116 extends along length L of emitter 114. A second pair of deflection electrodes 118 extends along width W of emitter 114. Adjacent surfaces 120 of electrode pairs 116 and 118 are oriented at an approximately 90° angle with respect to one another. Adjacent surfaces 120 form an electron beam passage area 122. Insulators 124 are disposed between backing member 112 and electrode pairs 116 and 118. However, cathode 110, unlike cathode 238, does not have a front member. Instead, electrode pairs 116 and 118 serve as a front member.

Backing member 112 controls the width and length of the focal spot. When differentially biased, i.e. when different voltages are applied to each electrode of an electrode pair, electrode pair 116 deflects the electron beam in the W-direction, such as in double sampling. Electrode pair 118 deflects the electrons in the L-direction. First electrode pair 116 also adjusts focal spot width and second electrodes pair 118 also adjusts focal spot length.

For certain applications, electrode pairs 282, 116, and 118 provide a negative voltage forward of emitters 272 and 114. The negative voltage reduces the electric fields at emitter surfaces, which provides current or mA modulation. "Current modulation" refers to an adjustment of the amount of electron emission current. Current modulation is achieved in some configurations by adjusting biasing voltages between backing member 112 and electrode pairs 116 and 118, similarly to the biasing between the front member 270 and the backing member 276 of cathode 238 described above. As a result of providing the negative voltage forward of the emitters 272 and 114, the width and length of the focal spots generated by the emitters 72 and 114 are reduced in size. To compensate for the reduction in focal spot width and length, i.e., to refocus electron beams generated therefrom, backing members 276 and 112 are operated at a more positive potential than is required for an unmodulated beam. As a result of providing sufficiently negative voltage forward of emitters 272 and 114, the electron flow can be cut off. This result is referred to as gridding. Gridding occurs when a negative voltage potential of approximately −4 kV to −7 kV exists between front members 270 and emitters 272 and 114.

Figure 7:
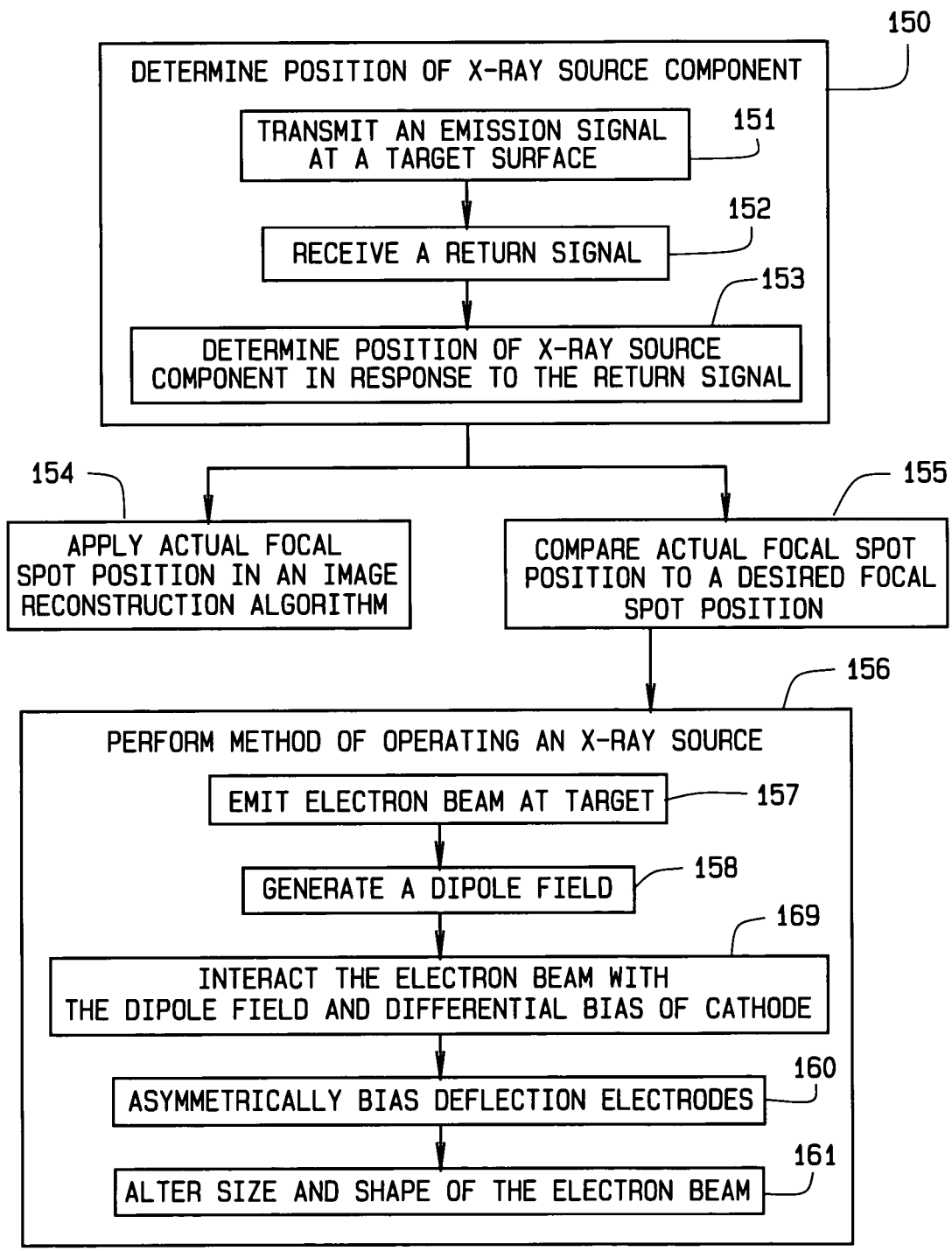
FIG. 7 is a logic flow diagram illustrating a configuration of the present invention for adjusting focal spot positioning including a method for determining position of an electromagnetic radiation source component and a method for operating an electromagnetic source.

Referring now to FIG. 7, a logic flow diagram illustrates various methods for adjusting focal spot positioning that include determining a position of an electromagnetic radiation source component and operating an electromagnetic source is shown. These methods can be performed automatically utilizing x-ray controller 28 and computer 36 under appropriate program control, with feedback from detector 18 as described herein. The technical effect of imaging system 10 is achieved by first, at 150, determining a position of an electromagnetic radiation source component. The position may be determined at selected time intervals or continuously depending upon the application and system conditions. In the following example, Z-position of target 242 is determined.

At 151, controller 28 transmits and probe 250 directs emission signal 252 at an electromagnetic radiation source component target surface, such as target 242. Emission signal 252 is directed from first end 262, incident upon target 242, and is reflected back to second end 64.

At 152, controller 28 receives return signal 254 in response to the reflection of the emission signal 252 on target 242.

At 153, upon receiving return signal 254, controller 28 determines a position of the electromagnetic radiation source component. Continuing the present example, controller 28 determines the z-position of target 242, which is approximately equal to position of focal spot 246.

In some configurations, at 154, controller 28 applies the determined actual focal spot position in performing a back-projection algorithm for CT image reconstruction. In some other configurations and at 155, controller 28 compares the actual focal spot position to a desired focal spot position for focal spot adjustment. In yet other configurations, controller 28 performs both functions 154 and 155. In still other configurations, controller 28 applies the determined actual focal spot position in other applications known in the art.

At 156, when the actual focal spot position is compared to a desired focal spot position and controller 28 determines that the focal spot position is outside a desired focal spot position range, the procedure at 156 is performed. The procedure at 156 may also be performed when wobbling the electron beam or for other reasons known in the art.

At 157, source 18 is operated in response to a difference between the actual focal spot position and the desired focal spot position.

At 158, emitter 274 emits an electron beam 298 from cathode 238 at target 242.

At 159, dipole field 297 is generated between emitter 274 and anode 244.

At 160, electron beam 298 interacts with dipole field 297 and the differential bias of cathode 238 or cathode 110.

At 161, deflection electrodes 282, 116, and 118 are asymmetrically biased to deflect the electron beam and adjust position of the focal spot.

At 162, dipole field 297 and the asymmetrical biasing of the deflection electrodes 282, 116, and 118 may be further modified to alter size and shape of the electron beam 298 and position of the focal spot 246. Upon completion of 161, in some configurations, controller 28 return to 150.

The above-described methods are intended to be illustrative. In other configurations, the various steps may be performed synchronously or in a different order, depending upon the application.

Figure 8:
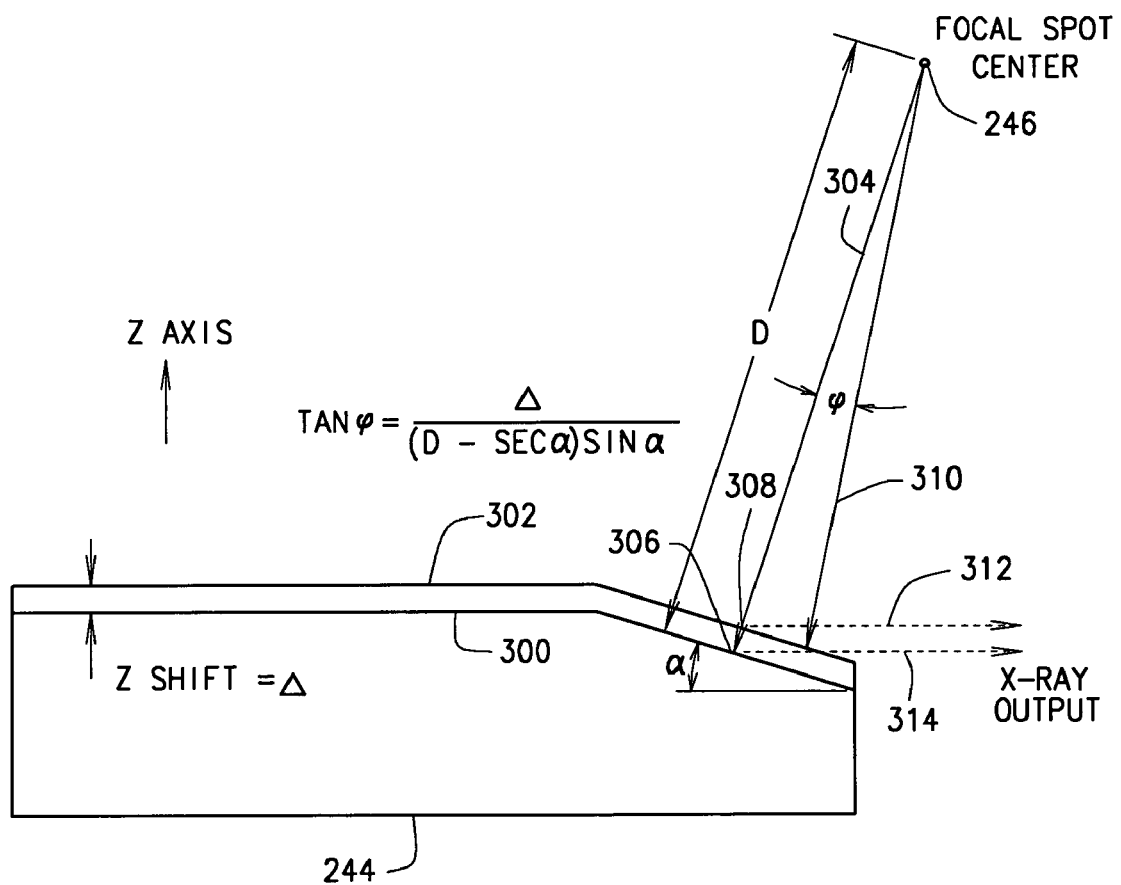
FIG. 8 is a geometrical representation of focal spot position compensation utilizing focal spot deflection in a z-axis direction.

Also in some configurations and referring to FIG. 8, it is anticipated that heating will affect anode 244 of x-ray tube 14. For example, and as shown in FIG. 8, anode 244 could move by an amount $\Delta$ (i.e., from anode surface position 300 to anode surface position 302) in the z-axis direction due to thermal effects. If focal spot 246 does not move, the apparent source of x-rays from a beam 304 appears to move up the target track from 306 to 308. To compensate for this effect, focal spot 246 is deflected by an amount $\tan(\phi) = \Delta/[(D - \sec \alpha)(\sin \alpha)]$, where $\Delta$ is the z-axis shift, D is the distance from focal spot center 246 to point 306 on anode 244, and $\alpha$ is the surface slope of anode 244. When thus compensated, the apparent x-ray source remains the same as before (i.e., the apparent x-ray source of deflected beam 310 is beam 312 rather than 314). In various configurations, compensation is maintained for the entire range of anode 244 positions encountered as a result of thermal and mechanical effects, so that collimator cams do not have to be adjusted during a scan to maintain the x-ray beam on detector 18 in the desired location.

To determine the amount of adjustment needed during a scan, a detector signal on "z-channels" (i.e., referring to FIG. 2, detector elements 20 near ends 316, 318 of detector 18 of a multi-row detector, only one row of which is illustrated in FIG. 2) are monitored to keep a z-ratio constant. (A "z-ratio" is a measure of intensities measured by detector elements 20 at one end, say 316, of detector 18 divided by a measure of intensities measured by detector elements 20 at the other end 318.) Focal spot 246 of x-ray source 14 is adjusted during a scan to keep this z-ratio constant. Thus, collimator cams need only be set to an initial, predefined position for a desired slice thickness. Moreover, focal spot 246 is maintained at the same length (as a function of mA), thereby relieving focal spot blooming problems.

Figure 9:
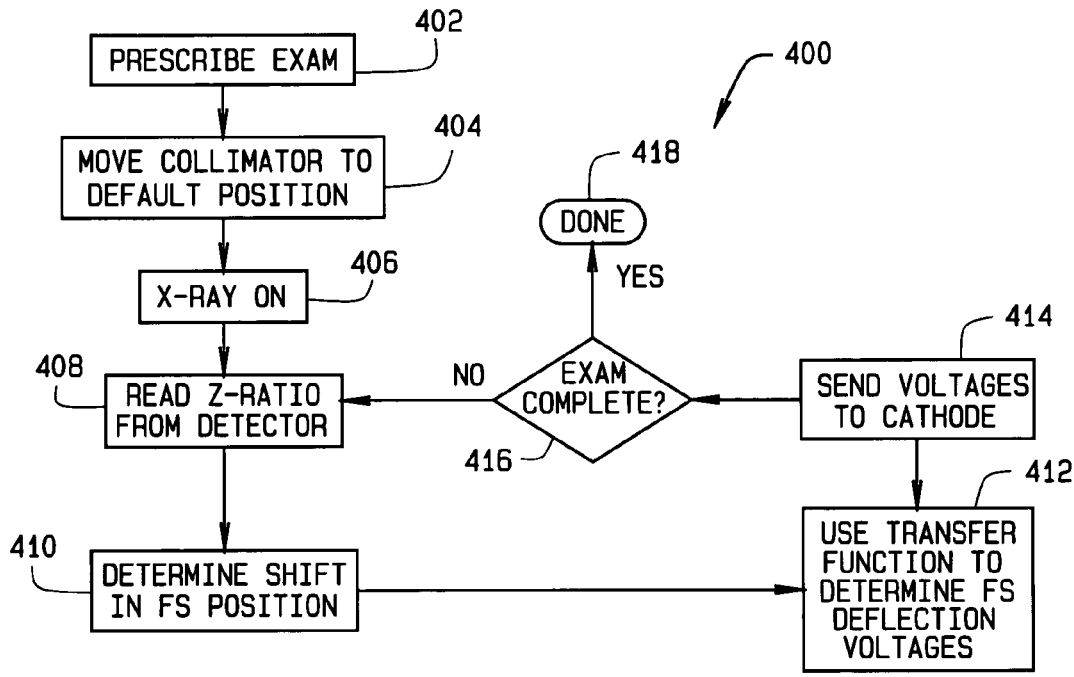
FIG. 9 is a flow chart for focal spot deflection representative of some configurations of the present invention.

More particularly, and referring to flow chart 400 shown in FIG. 9, a technical effect of imaging system 10 is achieved by a user first prescribing an exam at 402. Some configurations of the present invention then move a collimator to a default position at 404. The x-ray source is turned on at 406 to start the examination. During the examination, a z-ratio is read from the detector at 408. From this z-ratio, a shift in focal spot position is determined at 410. A previously determined transfer function determined using empirical measurements, physical laws, or both, is used to determine focal spot deflection voltages to compensate for shifts in focal spot position at 412. These voltages are sent to the x-ray source at 414. If the examination is complete at 416, the process described in flowchart 400 is deemed complete at 418. The computed tomographic system, including the x-ray source, can be turned off at 418 and/or readied for another examination. Otherwise, another z-ratio is read from the detector at 408, and a portion of the process continues until the examination is complete at 416.

Figure 10:
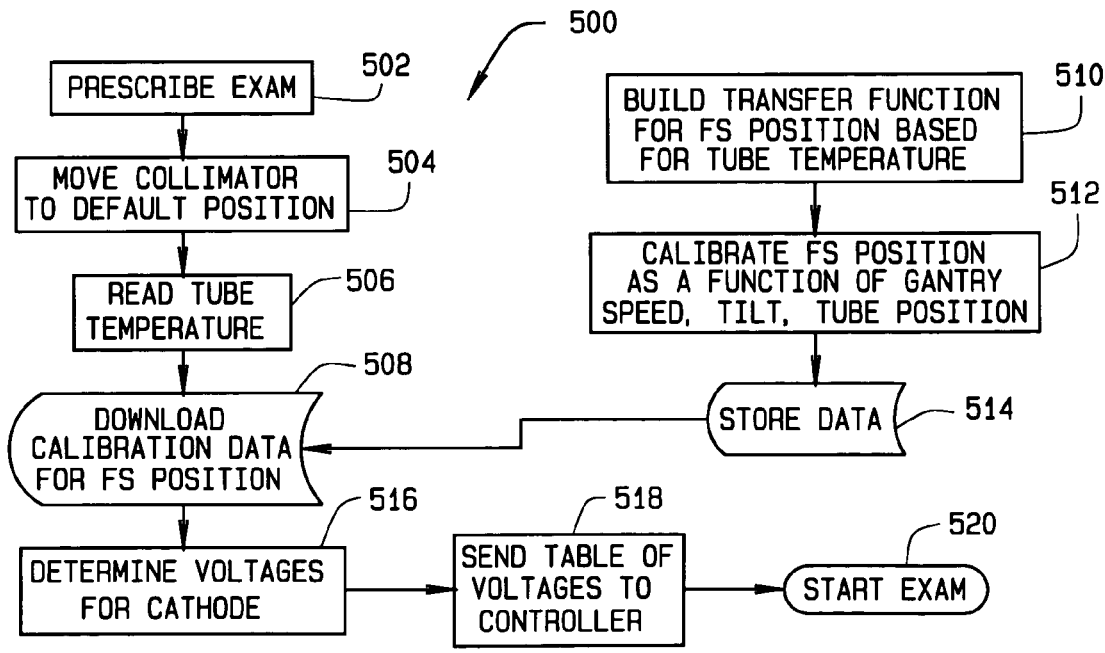
FIG. 10 is a flow chart for focal spot deflection representative of additional configurations of the present invention.

In some configurations of the present invention and referring to flow chart 500 of FIG. 10, transfer functions for focal spot 246 location are determined. These transfer functions are dependent upon system variables that may include gantry 12 speed, mA of current in x-ray tube 18, tilt, and thermal state. For example, in some configurations, focal spot position 246 as a function of thermal history of x-ray tube 18 is continuously determined. A calibration program characterizes focal spot 18 motion due to mechanical effects. Using the characterization thereby determined, an amount of deflection necessary to keep the apparent x-ray spot immobile is determined continuously.

More particularly, and referring to flow chart 500 in FIG. 10, a technical effect of imaging system 10 is achieved by a user prescribing an examination at 502. A collimator of imaging system 10 is then moved to a default position at 504 and x-ray tube 18 temperature is read at 506. At some time prior to the prescription of the examination, or at least in time for its use at 508, a transfer function is determined for focal spot position 246 as a function of tube temperature at 510. In addition, focal spot position 246 as a function of gantry 12 speed, tilt, and x-ray tube 18 position are calibrated at 512. Data from this calibration is stored in a memory at 514 (which may be, but need not be on a circuit card separate from controller 28) and calibration data for focal spot position 246 is downloaded at 508. Using the downloaded data, voltages for cathode 238 (or 110) of tube 18 are determined at 516 and a table of voltages is sent to controller 28 for cathode 238 (or 110) at 518. After the table is sent, the examination can be started at 520. Note that certain data storage and transfer steps shown in flowchart 500 of FIG. 10 (e.g., 514, 508, 518) are not required in configurations in which a card separate from controller 28 is not used to store data at 514.

Figure 11:
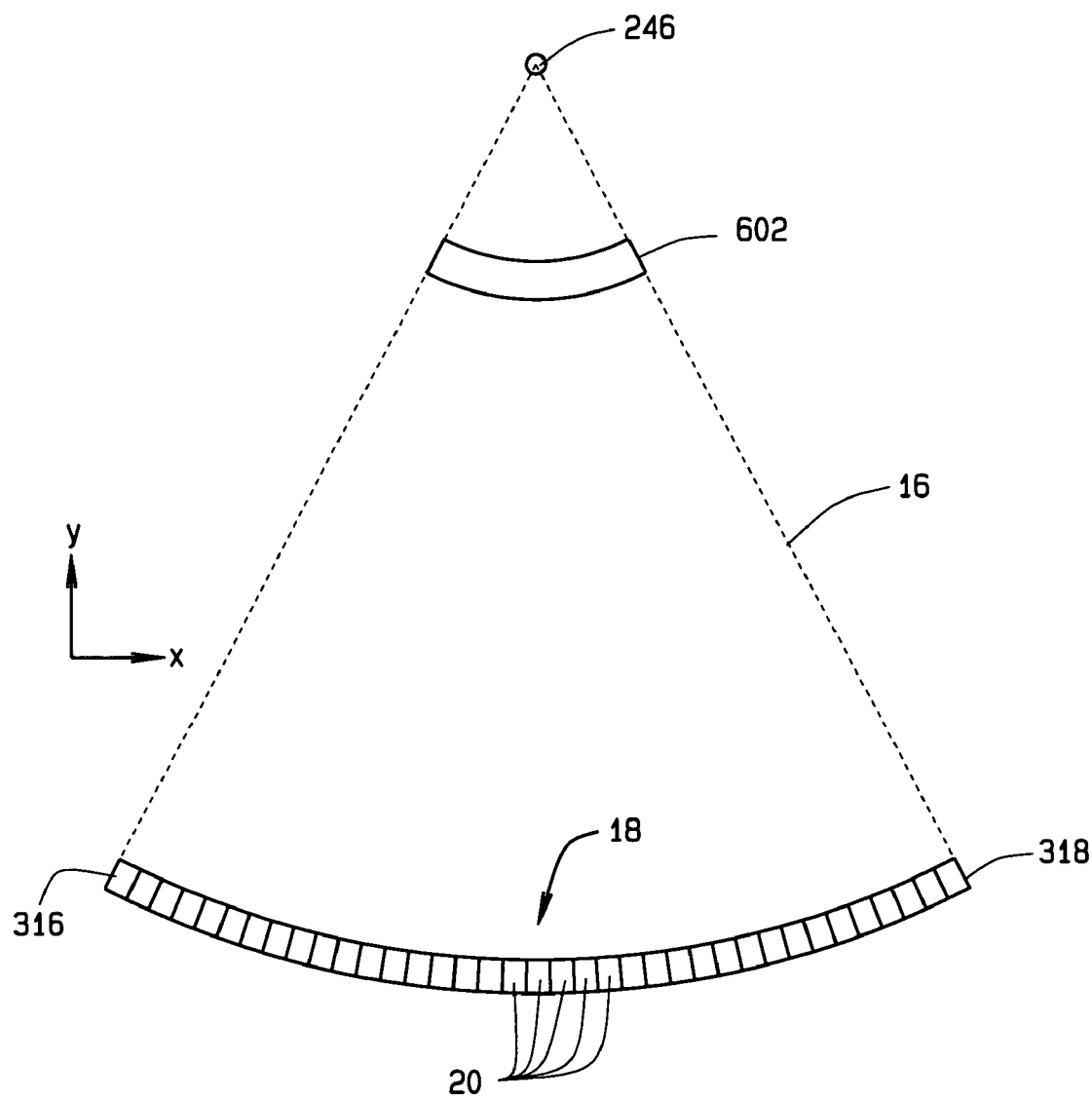
FIG. 11 is a simplified view, looking in the z-axis direction, of a collimator configuration of the present invention, showing curved collimator blades.
Figure 12:
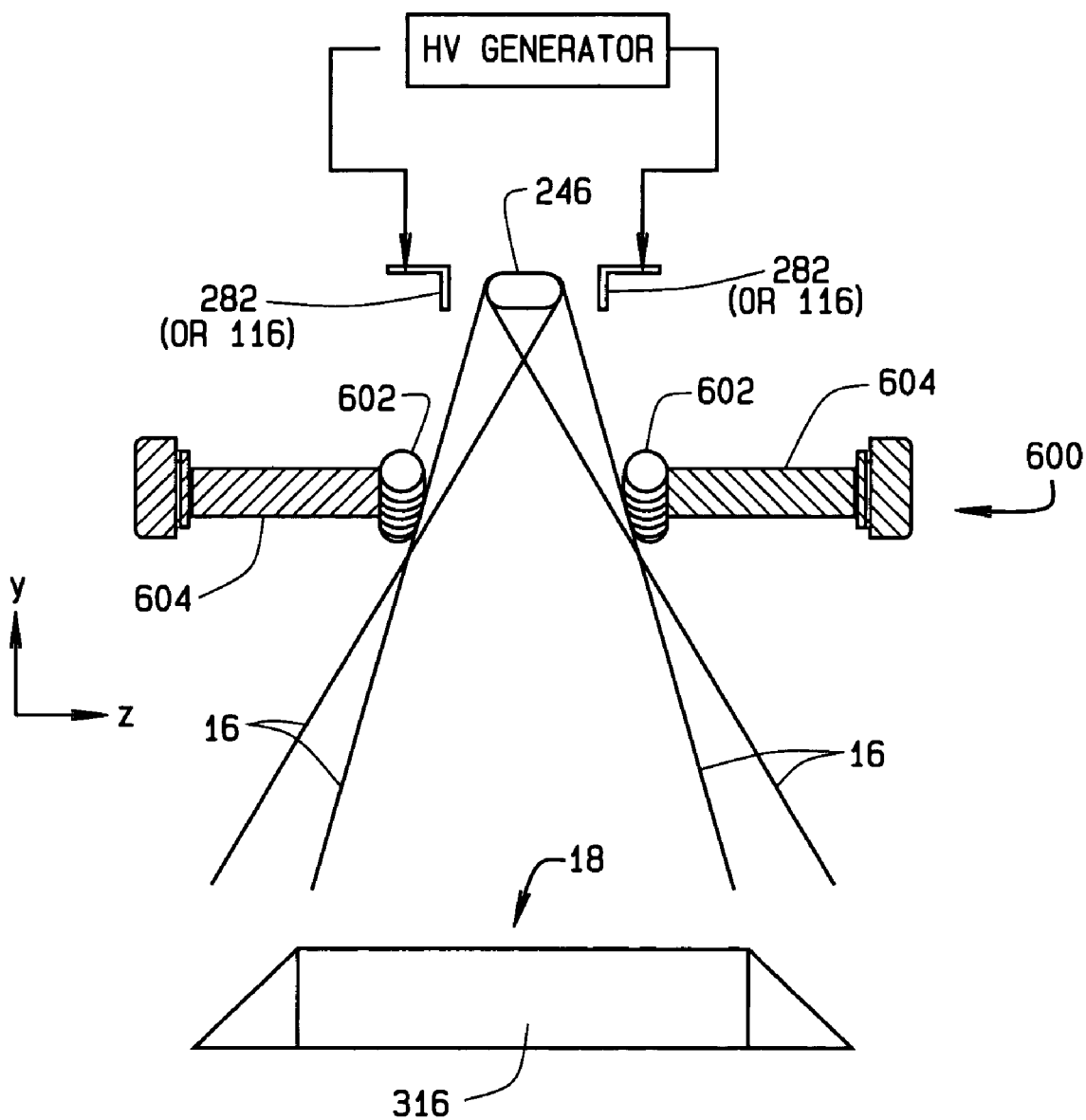
FIG. 12 is a simplified view, looking in the x-direction, of a collimator configuration of the present invention, showing curved collimator blades.

Utilizing cathode voltage control to compensate for deflection resulting from mechanical and thermal effects reduces or eliminates the need for collimators to provide rapid cam motion, thereby advantageously simplifying collimator design. Thus, some configurations of the present invention, such as those represented in the simplified views of FIGS. 11 and 12, incorporate collimators 600 having a curvature that matches that of detector 18 so that magnification is constant across detector 18. For example, FIG. 11 represents a simplified view of x-ray beam 16 in a plane perpendicular to the z-axis inside beam 16. The view looking in either direction perpendicular to this plane (i.e., in the z-axis direction) is the same. Only one row (or slice) of detector 18 is represented in FIG. 11. In some configurations of the present invention, a curved tube 602 is used as a collimator blade. The curvature of tube 602 advantageously matches that of detector array 18 so that magnification is the same all across detector array 18. Referring to FIGS. 11 and 12, in some configurations of the present invention, a collimator 600 comprises curved collimator blades such as curved tubes or cylinders 602 are mounted on ball screw drives 604 that slowly move collimator blades 602 to a default position. Such configurations provide a wide dynamic range between closed and wide positions, to the maximum permitted by the detector geometry.

In some configurations of the present invention, collimator blades 602 are not tubes but have edges curved proportionately in substantially the same shape as that of detector array 18 in the x-direction. In other configurations, different collimator blade shapes are used, but rapid cam motion is still avoided because of the ability to electrically compensate for mechanical and thermal deflection of focal spot 246.

In some configurations of the present invention, the electron beam of an x-ray tube is deflected magnetically utilizing a current through a pair of appropriately positioned deflection coils instead of a pair of deflection electrodes. In such configurations, a deflecting current through the pair of coils is utilized to deflect the electron beam in the z-axis direction. The deflection of the electron beam produced by the pair of deflection coils therefore results from a magnetic field rather than an electric field, but otherwise, the deflection current through the coils is analogous to the deflection voltage applied to the deflection electrodes. Appropriate modifications are therefore made in such configurations to determine and supply deflection currents rather than deflection voltages. Some configurations use both deflection coils and deflection electrodes to deflect the electron beam, and determine and adjust both deflection currents and deflection voltages. Therefore, the determination of at least one of a deflection current or a deflection voltage, or a combination thereof, is referred to herein as the determination of an "electronic deflection value"

Various configurations of the present invention advantageously utilize a z-axis modulation instead of or in addition to x-axis modulation. The z-axis modulation is used to perform z-axis tracking that does not require motion of cams in the collimator.

While the invention has been described in terms of various specific embodiments, those skilled in the art will recognize that the invention can be practiced with modification within the spirit and scope of the claims.

What is claimed is:

1. A method for adjusting a focal spot position during a scan of a computed tomography imaging system having a z-axis, wherein said computed tomography imaging system includes a detector array having a plurality of detector elements and an x-ray tube configured to direct an x-ray beam towards said detector through an object to be imaged, said method comprising:
    turning on the x-ray tube;
    reading a z-ratio from the detector;
    determining, utilizing the read z-ratio, a shift in a position of a focal spot of the x-ray tube;
    using a transfer function to determine an electronic deflection value; and
    applying the electronic deflection value to the x-ray tube as at least one of a deflection voltage or a deflection current to track the focal spot in the z-axis direction.

2. A method in accordance with claim 1 further comprising presetting a collimator of the computed tomography imaging system to a default position.

3. A method in accordance with claim 2 wherein presetting a collimator of the computed tomography imaging system comprises mechanically moving collimator blades.

4. A method in accordance with claim 1 further comprising determining whether an examination of an object is complete, and further comprising repeating said reading a z-ratio from the detector, determining a shift in a position of a focal spot of the x-ray tube, using a transfer function to determine a compensating electronic deflection value; and applying the electronic deflection value to the x-ray tube to at least partially track the focal spot in the z-axis direction until the examination is completed.

5. A method in accordance with claim 1 wherein said computed tomography imaging system is a volume computed tomography imaging system having a coverage between 20 to 200 mm at isocenter.

6. A method for adjusting a focal spot position during a scan of a computed tomography imaging system having a z-axis, wherein said computed tomography imaging system includes a detector array having a plurality of detector elements and an x-ray tube configured to direct an x-ray beam towards said detector through an object to be imaged, said method comprising:
    reading a temperature of the x-ray tube;
    obtaining calibration data for a focal spot position of the x-ray tube;
    obtaining a transfer function for focal spot position in accordance with x-ray tube temperature;
    utilizing the tube temperature and calibration data to determine voltages to be applied to a cathode of the x-ray tube; and
    applying the determined voltage to the cathode of the x-ray tube.

7. A method in accordance with claim 6 further comprising presetting a collimator of the computed tomography imaging system to a default position.

8. A method in accordance with claim 6 wherein the computed tomographic imaging system comprises a rotatable gantry and the x-ray tube and the detector are on the rotatable gantry, said method further comprising calibrating focal spot position as a function of gantry speed, tilt, and x-ray tube position.

9. A method in accordance with claim 8 wherein presetting a collimator of the computed tomography imaging system comprises mechanically moving collimator blades.

10. A method in accordance with claim 6 wherein said computed tomography imaging system is a volume computed tomography imaging system having a coverage between 20 to 200 mm at isocenter.

11. A computed tomography imaging system comprising:
    a detector array having a plurality of detector elements;
    an x-ray tube having a cathode and configured to direct an x-ray beam towards said detector array through an object to be imaged;
    wherein the x-ray tube and detector array are on a gantry defining a z-axis, and wherein said computed tomography system is configured to electronically adjust a focal spot of said x-ray tube in a z-axis direction to perform z-axis tracking; and
    a computer configured to determine a shift in focal spot position in accordance with z-ratio read from the detector and to utilize a transfer function to determine a cathode bias voltage for said x-ray tube to compensate for the focal spot position shift.

12. A system in accordance with claim 11 wherein said detector array includes z-channel elements, and to adjust a focal spot of said x-ray tube in a z-axis direction to perform z-axis tracking, said computed tomography imaging system is configured to adjust a voltage applied to said x-ray tube cathode.

13. A system in accordance with claim 12 wherein said x-ray tube further comprises an anode, and said system is further configured to maintain said focal spot at a position constant in the z-axis direction relative to a casing of the x-ray tube and the detector.

14. A system in accordance with claim 13 further comprising an x-ray collimator, and said system is configured to set said x-ray collimator to a predetermined initial position to collimate said x-ray beam in accordance with a specified slice thickness.

15. A system in accordance with claim 11 configured to continuously compensate for said focal spot position shift utilizing adjustments of said cathode voltage.

16. A system in accordance with claim 11 wherein said detector defines an x-direction and said detector is curved in said x-direction, and said system further comprises a collimator having collimator blades curved substantially in proportion to the curvature of said detector in said x-direction.

17. A computed tomography imaging system having a z-axis, and said system comprising a detector array having a plurality of detector elements and an x-ray tube configured to direct an x-ray beam towards said detector through an object to be imaged, comprising: a computer configured to:
   read a z-ratio from the detector using x-rays emitted from the x-ray tube;
   determine, utilizing the read z-ratio, a shift in a position of a focal spot of the x-ray tube;
   use a transfer function to determine an electronic deflection value; and
   apply the electronic deflection value to the x-ray tube as at least one of a deflection voltage or a deflection current to track the focal spot in the z-axis direction.

18. A system in accordance with claim 17 wherein said x-ray tube comprises a coil, said detector array includes z-channel elements, and to adjust a focal spot of said x-ray tube in a z-axis direction to perform z-axis tracking, said computed tomography imaging system is configured to adjust a current applied to said coil.

19. A system in accordance with claim 17 further configured to determine a temperature of said x-ray tube and to electronically adjust a focal spot of said x-ray tube in a z-axis direction in accordance with at least said determined temperature to perform z-axis tracking.

20. A system in accordance with claim 19 further configured to adjust said focal spot position in accordance with a speed of said gantry, tilt, and x-ray tube position.

* * * * *